United States Patent [19]

Chambers et al.

[11] Patent Number: 5,262,025
[45] Date of Patent: Nov. 16, 1993

[54] TELECHELIC TELOMERS OF CHLOROTRIFLUOROETHYLENE AND METHOD FOR PREPARING SAME

[75] Inventors: Richard D. Chambers, Whitesmocks; Martin P. Greenhall, Northfield, both of Great Britain; Antony P. Wright, Rhodes, Mich.

[73] Assignee: Dow Corning Corporation, Midland, Mich.

[21] Appl. No.: 745,308

[22] Filed: Aug. 15, 1991

[30] Foreign Application Priority Data

Apr. 20, 1991 [GB] United Kingdom ............... 9108509

[51] Int. Cl.$^5$ ............................................. C07C 17/00
[52] U.S. Cl. ......................... 204/157.94; 204/157.95; 204/158.11
[58] Field of Search ............. 204/157.94, 157.95, 204/158.11, 157.48

[56] References Cited

U.S. PATENT DOCUMENTS 3,051,764  8/1962  Hauptschein et al. ........ 204/157.95
3,089,911  5/1963  Hauptschein et al. ........ 204/158.11
3,816,286  6/1974  Haszeldine et al. ........... 204/158.11

OTHER PUBLICATIONS

Journal of Fluorine Chemistry [43 (1990), p. 199] by V. Tortelli and C. Tonelli.
J. Amer. Chem. Soc., 1951, 73, 1352.
Jacs 79, 2549 (1957) M. Hauptschein et al.
J.C.S. 4291 (1955) R. Haszeldine.
J.C.S. 4302 (1955) R. Haszeldine.

*Primary Examiner*—John Niebling
*Assistant Examiner*—Cybille Delacroix-Muirheid
*Attorney, Agent, or Firm*—Robert Spector

[57] ABSTRACT

Iodine terminated liquid telechelic telomers of chlorotrifluoroethylene (CTFE) containing an average of more than 1 CTFE unit per molecule are novel compounds. The telomers can be prepared by a photochemically initiated reaction between liquified CTFE and either elemental iodine or the telogen $ICF_2CFClI$ at temperatures below about 50° C.

10 Claims, No Drawings

TELECHELIC TELOMERS OF CHLOROTRIFLUOROETHYLENE AND METHOD FOR PREPARING SAME

BACKGROUND OF THE INVENTION

1. Field of the Invention

This invention relates to telomers of chlorotrifluoroethylene. More particularly, this invention relates to novel iodine-terminated telechelic telomers of chlorotrifluoroethylene that are prepared from elemental iodine and chlorotrifluoroethylene.

2. Background Information

Bifunctional or telechelic telomers derived from fluorinated olefins are known and are becoming increasingly important based on their desirable properties, particularly insolubility in organic liquids and thermal stability. For example, telomers of tetrafluoroethylene prepared by reacting $ICF_2CF_2I$ with $CF_2=CF_2$ are reported by V. Tortelli and C. Tonelli in the Journal of Fluorine Chemistry [43 (1990), p. 199].

Addition reaction products of chlorotrifluoroethylene (CTFE) with fluorine, chlorine, bromine and the interhalogens BrF, IF, ICl, and IBr are reported and have been well characterized in the chemical literature. These products have been prepared by heating or the use of free radical initiators such as peroxides. Photochemical initiation of the reactions is not reported.

The reaction of chlorotrifluoroethylene with elemental iodine is reported by J. T. Barr et al. (J. Amer. Chem. Soc., 1951, 73, 1352. A mixture containing equal weights of the reactants was sealed in a glass tube and allowed to stand for several days under ambient conditions. The resultant liquid product, thought to be 1-chloro-1,2,2-trifluoro-1,2-diiodoethane, was distilled in 30-35% yield and boiled from 54°-55° C. under a pressure of 20 mm Hg. The product decomposed upon standing to yield iodine and no other isolatable product, and was not sufficiently stable to be analyzed. By comparison, the reaction product of chlorotrifluoroethylene with iodine monochloride was stable and was characterized as $CF_2ClCFClI$.

M. Hauptschein et al. [JACS 79, 2549 (1957)] describes the reaction of chlorotrifluoroethylene with the stable telogen reported by Barr, namely $CF_2ClCFClI$, at a temperature of 200° C. using a spiral tube reactor that minimized contact time between the reactants. The product contained 22 weight percent each of the telomers $CF_2ClCFCl(C_2F_3Cl)_nI$ where the value of n was 1, 2, or 3 and 33 weight percent of telomers wherein n was 4 or greater.

R. Haszeldine [J.C.S. 4291 (1955)] describes the telomerization of chlorotrifluoroethylene in the presence of the telogen $ClCF_2CFClI$ and ultraviolet light or heat to yield telomers. Telomers containing up to 20 repeating units per molecule are characterized as liquids. The author proposes using peroxides as the free radical source for large scale reactions.

The article by Haszeldine makes no mention of using the bifunctional telogen $ICF_2CFClI$, reported as unstable in the aforementioned article by Barr et al., to initiate the telomerization of chlorotrifluoroethylene (CTFE). Based on the instability of this telogen reported by Barr et al. it is unlikely that one would consider substituting it for the telogen $ClCF_2CFClI$ reported by Haszeldine.

The present inventor therefore considered it surprising to discover that when iodine is combined with more than an equimolar amount of CTFE the iodine will react substantially completely in the presence of ultraviolet or visible radiation to initially produce the telogen reported by Barr et al. Upon further exposure to radiation the telogen is gradually converted to stable telomers represented by the general formula $I(CF_2CFCl)_nI$, where the average value of n is greater than 1. The value of n for a particular product is determined by the reaction conditions, specifically the type of radiation, exposure time, and the reaction temperature.

The bifunctional telomers of CTFE can be reacted with fluorine, olefins or fluoroolefins to obtain products in the form of liquids, solids and greases.

The present inventor also discovered that the bifunctional telogen $ICF_2CFClI$ can be isolated if the reaction of CTFE and iodine is conducted in the presence of visible light or gamma radiation. Contrary to the teaching of Barr et al. the telogen is stable when stored in the dark at temperatures below about 30° C.

SUMMARY OF THE INVENTION

Iodine terminated telechelic telomers of chlorotrifluoroethylene (CTFE) containing an average of more than one CTFE unit per molecule are novel compounds. The telomers can be prepared by a photochemically initiated reaction between CTFE and either iodine or the telogen $ICF_2CFClI$ at temperatures below about 50° C.

DETAILED DESCRIPTION OF THE INVENTION

This invention provides telechelic telomers of the average formula $I(CH_2CH_2)_q(R^1)_m(CF_2CFCl)_n(R^1)_p(CH_2CH_2)_qI$, where $R^1$ is selected from the group consisting of fluoroalkylene radicals containing from 2 to 5 carbon atoms and radicals of the formula $-CF_2CF(OR_f)-$ where $R_f$ represents a perfluoroalkyl radical containing 1 to 2 carbon atoms, the average value of n is greater than 1 and the average values of m, p and q are individually 0 or a positive number.

This invention also provides a method for preparing an iodine terminated telechelic telomer of chlorotrifluoroethylene, said method comprising the steps of 1) exposing a mixture of elemental iodine and a stoichiometric excess of liquified chlorotrifluoroethylene to visible or ultraviolet light while maintaining said mixture at a temperature of from 20° to 50° C. for a period of time sufficient to prepare a telomer containing an average of more than one chlorotrifluoroethylene unit per molecule, and 2) isolating said telomer from the mixture.

Alternatively, the iodine can be replaced by the telogen $ICF_2CFClI$. The telogen can be prepared by reacting elemental iodine with CTFE under the same conditions used to prepare the present telomers, but for shorter periods of time. The telogen can also be prepared by exposing a mixture of iodine and CTFE to gamma radiation.

The present invention is based on the unexpected ability of elemental iodine and a stoichiometric excess of chlorotrifluoroethylene, referred to hereinafter as CTFE, to react in the presence of visible or ultraviolet light to form stable telechelic telomers. The light preferably exhibits a wavelength within the range of from 300 to 800 nanometers.

The present telomers are characterized as comprising 1) an average of more than 1 repeating unit per molecule derived from CTFE, and 2) an iodine atom at each of the two terminal positions. The term "telechelic" refers to the bifunctional nature of the present telomers resulting from the presence of the two iodine atoms.

The average number of repeating units derived from CTFE, represented by n in the preceding formula, is greater than 1. This value can be as high as about 300, however this value is preferably from 2 to about 10, this preference being based on the physical state of these telomers, which are relatively high boiling liquids under ambient conditions of temperature and pressure. Liquids are preferred for many end use applications of CTFE telomers.

For some end use applications the properties of the present iodine-terminated telechelic telomers derived from CTFE are modified by reacting the telomers with fluorine or with ethylenically unsaturated fluorinated and/or non-fluorinated compounds such as ethylene, hexafluoropropene, tetrafluoroethylene and perfluorinated vinylalkyl ethers wherein the alkyl portion of the ether contains 1 or 2 carbon atoms.

Preparation of Telechelic CTFE Telomers

The present telomers are obtained by the reaction of elemental iodine with a stoichiometric excess of liquified CTFE in the presence of visible or ultraviolet light. In the presence of excess CTFE the initially formed telogen reacts to form the telomers of this invention.

The reaction of iodine and CTFE to form the telogen is an equilibrium that can be represented by the equation 1

$$CF_2=CFCl + I_2 \rightarrow ICF_2CFClI \quad (1)$$

The equilibrium constant for the reaction at room temperature is about 0.22. Because the concentration of the iodine is limited by it solubility in the reaction mixture, it is therefore necessary to use more than the required stoichiometric amount of CTFE to drive the reaction toward formation of the desired telogen. The term "stoichiometric amount" with reference to equation 1 is one mole of iodine per mole of chlorotrifluoroethylene.

At temperatures below about 0° C. the solubility of iodine in liquid CTFE becomes so low that the rate of conversion of iodine to the telogen is slowed. At temperatures above about 50° C. the equilibrium constant (K) for the reaction decreases.

The factors influencing the rate of telogen formation appear to be the rate of solubilization of the iodine in the CTFE and the intensity of the radiation. Improving the distribution of the solid iodine throughout the reaction mixture is one means to increase the rate of solubilization and hence the rate of telomer formation. This can be achieved by agitating the liquid CTFE using mechanical means or allowing the CTFE to boil by cooling the portion of the reactor occupied by vaporized CTFE.

Preferred conditions for preparation of the telogen are a reaction temperature of from 20° to about 40° C. using a molar ratio of CTFE to iodine of from 6:1 to 30:1.

The exposure time required to convert substantially all of the iodine to telogen is at least partially dependent on the wavelength and intensity of the radiation to which the reaction mixture is exposed. Using sunlight, exposure times of from about 100 to about 200 hours should be sufficient. The course of the reaction can conveniently be followed by observing the amount of unreacted iodine remaining in the mixture.

The use of ultraviolet light for formation of the telogen is preferred based on the somewhat slower rate of this reaction in the presence of visible light. Because the rate of telogen formation is limited by the solubilization rate of the iodine, from the viewpoint of energy conservation it may be desirable to first prepare the telogen in the presence of visible light, particularly sunlight, and then employ ultraviolet light to react the telogen with additional CTFE to form the present telomers.

Because the rate of telomerization appears to be considerably slower than the rate of telogen formation when the reaction of iodine with excess CTFE is carried out in the presence of visible light or gamma radiation from radioactive cobalt rather than ultraviolet radiation, by conducting the reaction under conditions less favorable for the telomerization reaction it is possible to isolate the telogen in the absence of substantial amounts of telomer.

When gamma radiation is used to initiate reaction of elemental iodine and CTFE, the telogen can be isolated in the absence of substantial amounts of telomer.

The reaction of the initially formed telogen with additional CTFE in the presence of visible or ultraviolet radiation to form the present telomers can be represented by equation 2.

$$ICF_2CFClI + nCF_2=CFCl \rightarrow I(CF_2CFCl)_{n+1}I \quad (2)$$

This does not appear to be an equilibrium reaction. The resultant telomers are stable under conditions that decompose the telogen.

Depending upon the intensity of the radiation at the reaction mixture and the desired degree of polymerization, represented by the value for n in the foregoing equation 2, the present inventors have found that exposure times of from 48 to about 300 hours are sufficient to react substantially all of the telogen. It appears that the average value of n increases with longer exposure times.

Any convenient source of ultraviolet radiation can be used to prepare the telogens and telomers. Mercury vapor lamps exhibiting maximum radiation in the range from 250 to about 350 nm are preferred based on their cost and availability.

At wavelengths below about 300 nm the telomer partially decomposes to yield $CF_2=CF(CF_2CFCl)_nI$ with the generation of ICl as a by-product. ICl will react with CTFE in the same manner as elemental iodine, however the resultant telomer may be less stable than the present telomers due to the presence of the $ClCF_2CFCl—$ group that can undergo dechlorination. It is therefore preferable to use reactors formed from Pyrex ® glass rather than quartz, based on the ability of quartz and the inability of Pyrex glass to transmit wavelengths of radiation below about 300 nm.

The wavelength range of from 300 to about 500 nm. appears optimum with regard to accelerating the rate at which the telogen ICF2CFClI reacts with CTFE to form the present telomers while avoiding decomposition of the telomer.

Subsequent Reaction of the CTFE Telomer With Fluorine or Olefins

For certain end use applications the presence of terminal iodine atoms and/or a unit derived from CTFE is undesirable. Replacement of the iodine atoms with fluorine can be achieved by reacting the telomer with elemental fluorine. A substantially quantitative replacement of the iodine atoms occurs when fluorine is bubbled through the liquid telomer at a temperature of from 0° C. to about ambient. Telomers containing 9 or fewer repeating units yielded liquid fluorinated products. Under the same reaction conditions higher molecular weight telomers formed greases.

The present telomers react with fluorinated ethylenically unsaturated organic compounds such as tetrafluoroethylene (TFE), 1,1-difluoroethylene, and perfluorinated alkylvinyl ethers at temperature of from about 150° to about 250° C. The alkyl portion of the perfluorinated ethers preferably contains 1 or 2 carbon atoms. The —CFClI terminal group (a) of the telomer appears considerably more reactive with these fluorinated compounds than the ICF$_2$— terminal group (b).

The present inventors found that after 16 hours of reaction at 165° C. 82% of the telomer reacted with TFE to yield I(CF$_2$CFCl)$_n$CF$_2$CF$_2$I.

At a temperature of 220° C. 90% of the (a) terminal groups reacted to form I(CF$_2$CFCl)$_n$(CF$_2$CF$_2$)$_m$I, where the value of m is about 1.4, indicating the reaction of more than one molecule of tetrafluoroethylene per molecule of telomer.

Tetrafluoroethylene is known to react with iodine terminated fluorocarbon telomers to yield copolymers containing from about 10 to about 300 or more units derived from this monomer. These copolymers range in viscosity from viscous oils to greases to solid materials.

Hexafluoropropene reacts with the present telomers at a slower rate than tetrafluoroethylene (TFE) and other fluorinated ethylenically unsaturated compounds. As with TFE, reaction at terminal group (a) was favored.

Both the present CTFE telomers and reaction products of these telomers with perfluorinated ethylenically unsaturated compounds will react with ethylene or other ethylenically unsaturated hydrocarbons in the presence of a platinum catalyst. The reaction product of one mole of telomer with two moles of ethylene exhibits the formula ICH$_2$CH$_2$(CF$_2$CFCl)n(CH$_2$CH$_2$I In one experiment 44% of terminal group (a) and 22% of terminal group (b) reacted after 19 hours at 70° C. It is believed that the incomplete reaction was caused by elemental iodine poisoning the platinum catalyst. Poisoning of the catalyst could be avoided by ensuring that all of the residual telogen was removed from the reactor prior to reaction of the telomer with ethylene.

Telomers containing hydrogen and chlorine on adjacent carbon atoms may undergo dehydrochlorination when heated at temperatures above about 150° C. Because this reaction adversely affects the thermal stability and physical properties of the resultant telomer, when the telomers are reacted, also referred to as "endcapped", with ethylene or other olefin containing hydrogen on at least one of the ethylenically unsaturated carbon atoms, it is desirable to ensure the absence of dehydrochlorination by first reacting the telomer with a perfluorinated ethylenically unsaturated compound such as hexafluoropropene or tetrafluoroethylene, and then reacting the resultant telomer with the olefin.

EXAMPLES

The following examples describe preferred embodiments of the present telomers and the method for preparing these telomers, and should therefore not be considered as limiting the scope of the accompanying claims. Unless otherwise specified all parts and percentages are by weight.

Description of Equipment

One type of Carius tube (I) used for the telomerization reactions had a capacity of 2.4 ml and was prepared from 8.5 inch (21.6 cm) sections of Pyrex ® glass tubing having an outside diameter of 8 mm and a wall thickness of 2.0 mm. A second type of Carius tube (II) had a capacity of 75 ml, a length of 9 inches (22.9 cm) and was equipped with a Teflon Rotoflow ® valve. A third type of Carius tube was fabricated from quartz.

The ultraviolet light sources were a model RPR-208 Rayonet ® reactor equipped with either a low pressure 254 lamp (1), a medium pressure 254–600 nanometer lamp (2) or (3) a 1000 watt Hanovia ® medium pressure mercury lamp.

The telomers were characterized by gas liquid chromatography (GLC) using a 15 meter SE-30 column, 10 psi (69 kPa) of back pressure and a temperature profile of 5 minutes at 40° C. followed by an increase of 10° C./minute to 270° C.

Some of the telomers were characterized using a Brinker $^{19}$F nuclear magnetic resonance spectrometer operating at a frequency of 235 megahertz.

EXAMPLE 1

This example demonstrates the preparation of telomers by the irradiation with ultraviolet light of mixtures containing various proportions of elemental iodine and chlorotrifluoroethylene (CTFE). The quantities of iodine and CTFE listed in Table 1 were sealed in a type I or type II Carius tube and irradiated with one of the three ultraviolet light sources for the time period specified in Table 1. The tube was then opened and the unreacted CTFE recovered and weighed. The liquid remaining in the tube was then analyzed using GLC and $^{19}$F nuclear magnetic resonance to determine the relative concentrations of the various telomers present. The results of these analyses are summarized in Table 1.

TABLE 1

| Sample No. | g. charged/g. CTFE | recovered I$_2$ | Mole Ratio | Conditions UV Source/Hrs. | Prod. Wt. (g) | n = 1/2/3/4 |
|---|---|---|---|---|---|---|
| 1 | 44.3/41.5 | 4.64/0 | 20 | 1/48 | 7.3 | 1.5/1/tr/0 |
| 2 | 65.5/53.91 | 52.8/26.5 | 2.7 | 3$^b$/72 | 37.5 | 30/1/0/0 |
| 3 | 62.7/52.6 | 10.9/0 | 13 | 1/168 | 20.5 | 1.6/1/0.7/tr$^a$ |
| 4 | 64.3/ND | 19.9/1.3 | 7 | 1/156$^c$ | 40.2 | 2.1/1/0.56/0.32 |
| 5 | 59/43.2 | 26.1/5.9 | 4.9 | 2/288 | 34.6 | 2.1/1/0.6/0.3 |
| 6 | 39.24/ND | 10.17/0 | 8.4 | 1/200 | 16.6 | 4/1/0.7/tr/tr |

TABLE 1-continued

| Sample No. | g. charged/g. CTFE | recovered $I_2$ | Mole Ratio | Conditions UV Source/Hrs. | Prod. Wt. (g) | n = 1/2/3/4 |
|---|---|---|---|---|---|---|
| 7 | 58.9/39.6 | 21.2/0 | 6.1 | $3^d$/160 | 39.5 | 4.6/1/tr |

$^a$tr = trace
$^b$Air circulation reduced power reaching sample to 100 watts.
$^c$Sample heated at 40° C. throughout exposure period
$^d$Sample exposed using a quartz Carius tube
ND Not determined

EXAMPLE 2

This example demonstrates the ability of lower molecular weight telomers prepared by irradiating mixtures of CTFE and iodine with ultraviolet light to be separated into low and high molecular weight fractions. A portion of the liquid telomer prepared as sample 3 in Example 1 was placed under high vacuum (0.05 mm Hg) for three hours. The residue exhibited a consistency between that of a liquid and a grease and was considerably more viscous than the initial sample 3. Analysis of the product by gas chromatography and $^{19}F$ NMR indicated an average of 4 CTFE units per molecule.

EXAMPLE 3

This example demonstrates the ability of an iodine-terminated telogen of CTFE to undergo reaction with additional CTFE in the presence of ultraviolet light to form telomers.

A mixture of 124.46 g (1.07 moles) of CTFE and 72.68 g (0.29 mole) of iodine was placed in a Carius tube. The tube was then sealed and rotated end-over-end for five days close to a source of gamma radiation. The tube was then opened and 102.58 g (0.88 mole) of CTFE were recovered together with 45.7 g of a purple liquid. Analysis using gas liquid chromatography indicated that the liquid was substantially pure telogen, $ICF_2CFCII$ (0.12 mole), containing a small amount of dissolved iodine.

A glass Carius tube was charged with 4.63 g (12.5 mmol) of the telogen and 39.9 (342 mmol) of CTFE. The tube was then sealed and irradiated for three days under the full power of the ultraviolet light generated by a 1000 watt Hanovia(R) medium pressure lamp. The tube was then opened and 34.33 g of CTFE were recovered together with 7.67 g of a liquid and 2.42 g of a solid residue that was subsequently shown to be mostly iodine. Analysis using $^{19}F$ NMR indicated that the liquid product was a telomer containing an average of 5.0 CTFE units per molecule.

In a similar experiment 58.7 g of CTFE and 14.9 g of iodine (mole ratio of CTFE to iodine = 8.6) was exposed to full sunlight for seven days, at which time all of the iodine appeared to have dissolved. The resultant colored solution was then irradiated at a distance of about 25 cm from a 1000 watt medium pressure mercury vapor lamp for seven days, at which time the color of the initial solution was fading. 20.4 g of CTFE was recovered together with 56.2 g of a viscous purple liquid.

The $^{19}F$ nuclear magnetic resonance spectrum was consistent with a telomer containing an average of 6.0 CTFE units per molecule.

EXAMPLE 4

This example demonstrates the inability of hexafluoropropene to undergo a reaction with elemental iodine in the presence of ultraviolet light.

Iodine (0.19 g, 0.7 mmol) and hexafluoropropene (1.81 g, 12 mmol) were sealed into a Pyrex Carius tube. The tube was then rotated end-over-end at a distance of approximately 30 cm from a 1000 watt medium pressure mercury lamp for 42 hours. At the end of this time the tube contained iodine and a free-flowing liquid that evaporated completely under ambient conditions when the tube was opened. The liquid was assumed to be unreacted hexafluoropropene.

EXAMPLE 5

This example demonstrates the ability of chlorotrifluoroethylene to telomerize in the presence of iodine and sunlight.

A 75 cc-capacity Carius tube was charged with 14.8 g. of iodine crystals. After being evacuated using a vacuum line while being cooled to $-78$ degrees C., the tube was charged with 61.5 grams of chlorotrifluoroethylene. The tube was then sealed, removed from the vacuum line and exposed to full sunlight for 14 days. At the end of this exposure period the tube contained a viscous liquid and no iodine crystals. The tube was then opened and the contents allowed to flow into a container. 9.0 grams of chlorotrifluoroethylene evaporate, leaving 66.1 g. of a transparent pink grease that converted to a flowable oil at 42 degrees C. This was equivalent to an 85% conversion of the initial chlorotrifluoroethylene.

Based on the $^{19}F$ nuclear magnetic resonance spectrum the product was assigned the average formula $I(CF2CFCl)_{8.26}I$. This spectrum exhibited maxima at the following chemical shifts: 49–54 ppm=m, 2.45 F; 65–71 ppm=m, 0.77 F; 96–104 ppm=m, 2.2 F; 105–11 ppm=m, 18.3 F; 115–122 ppm=m, 1.2 F; and 123–130 ppm=m, 6.5 F.

That which is claimed is:

1. A method for preparing an iodine terminated telechelic telomer of chlorotrifluoroethylene, said method comprising the steps of
    1) exposing a mixture comprising a stoichiometric excess of liquified chlorotrifluoroethylene and at least one reactant selected from the group consisting of elemental iodine and the telogen $ICF_2CFClI$ to visible or ultraviolet light while maintaining said mixture at a temperature of from 0° to 50° C. for a period of time sufficient to prepare a telomer containing an average of more than one chlorotrifluoroethylene unit per molecule, and
    2) isolating said telomer from the reaction mixture.

2. A method according to claim 1 where the wavelength of said light is from 300 to 800 nanometers, said telomer contains an average of from 2 to 10 repeating units per molecule and is a liquid at 25° C. under atmospheric pressure, and said temperature is from 0° to 50° C.

3. A method according to claim 2 where said wavelength is from 300 to 500 nanometers.

4. A method according to claim 1 where said reactant is elemental iodine, the molar ratio of chlorotrifluoroethylene to iodine is from 6:1 to 30:1, inclusive, and said temperature is from 20° to 40° C.

5. A method according to claim 1 where said reactant is said telogen and is prepared by exposing a mixture of chlorotrifluoroethylene and elemental iodine to visible light or gamma radiation at a temperature of from 20° to 40° C. for a period of time sufficient to form said telogen.

6. A method according to claim 5 where the molar ratio of chlorotrifluoroethylene to said telogen is from 6:1 to 30:1, inclusive, and the wavelength of said light is from 300 to 800 nanometers.

7. A method according to claim 6 where the wavelength of said light is from 300 to 500 nanometers.

8. A method according to claim 1 where said telomer is subsequently reacted with at least one reactant selected from the group consisting of ethylene, tetrafluoroethylene and hexafluoropropene.

9. A method according to claim 8 where said telomer is first reacted with tetrafluoroethylene or hexafluoropropene, followed by a reaction with ethylene.

10. A method according to claim 1 where said telomer is subsequently reacted with fluorine to replace substantially all of the terminal iodine atoms of said telomer with fluorine atoms.

* * * * *